US006210879B1

(12) United States Patent
Meloni et al.

(10) Patent No.: US 6,210,879 B1
(45) Date of Patent: Apr. 3, 2001

(54) METHOD FOR DIAGNOSING SCHIZOPHRENIA

(75) Inventors: Rolando Meloni, Paris; Claudine Laurent, Saint Cloud; Jacques Mallet, Paris, all of (FR)

(73) Assignee: Rhone-Poulenc Rorer S.A., Antony Cedex (FR)

( * ) Notice: Subject to any disclaimer, the term of this patent is extended or adjusted under 35 U.S.C. 154(b) by 0 days.

(21) Appl. No.: 08/930,117

(22) PCT Filed: Apr. 29, 1996

(86) PCT No.: PCT/FR96/00650

§ 371 Date: Dec. 22, 1997

§ 102(e) Date: Dec. 22, 1997

(87) PCT Pub. No.: WO96/34980

PCT Pub. Date: Nov. 7, 1996

(30) Foreign Application Priority Data

May 3, 1995  (FR) .................................................. 95 05264

(51) Int. Cl.⁷ .............................. C12Q 1/68; C12P 19/34; G01N 33/00
(52) U.S. Cl. ........................... 435/6; 435/91.1; 435/91.2; 435/270; 204/456; 436/94
(58) Field of Search .............................. 435/6, 91.1, 91.2, 435/183, 810, 270; 536/23.1, 24.3, 24.37, 25.3; 935/1, 8, 76, 77; 204/456; 436/94

(56) References Cited

FOREIGN PATENT DOCUMENTS

WO 94/03640    2/1994  (WO) .

OTHER PUBLICATIONS

Meloni et al., A rare allele of microsatellite located in the tyrosine hydroxylase gene found in schizophrenic patients, C.R. Acad. Sci. Ser. III, 318, 803–809 (1995).

Meloni et al., Association of manic–depressibe illness with tyrosine hydroxylase microsatellite marker, The Lancet, 345, 932 (1995).

Edwards et al., Genetic Variation at Five Trimeric and Tetrameric Tandem Repeat Loci in Four Human Population Groups, Genomics 12, 241–253 (1992).

Byerley et al., Tyrosine hydroxlase gene not linked to schizophrenia in nine pedigrees, Psyschiatric Genetics 3, 29–31 (1993).

Wei et al., Association of polymorphic VNTR region in the first intron of the human TH gene with disturbances of the catecholamine pathway in schizophrenia, Psychiatric Genetics, 5, 83–88 (1995).

Primary Examiner—Bradley L. Sisson

(57) ABSTRACT

The present invention relates to a method for diagnosing schizophrenia, said method being based on the detection in vitro of the presence of the allele Ep of the microsatellite HUNTH01 in the gene TH. The invention also relates to the primers used for implementing said method.

21 Claims, 3 Drawing Sheets

Figure 2A:
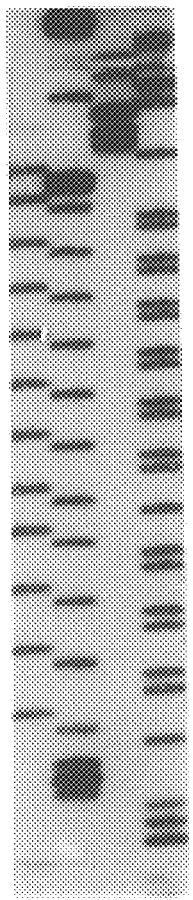

CTTGAATCTT AACGATCGGA ATGTGGAAAC AAATCCATCC AAAAAATCCA
AGATGGCCAG AGGTCCCCGG CTGCTGCACC CAGCCCCAC CCTACTCCCA
CCTGCCCCTG CCTCCCTCTG CCCCAGCTGC CTAGTCAGC ACCCCAACCA
GCCTGCCTGC TTGGGGAGGC AGCCCCAAGG CCCTTCCCAG GCTCTAGCAG
CAGCTCATGG TGGGGGGTCC TG[1],[3]GGCAAATA GGGGGCAAAA TTCAAAGGGT
ATCTGGGCTC TGGGGTGATT CCCATTGGCC T[5]GTTCCTCCC TTATTTCCCT
CATTCATTCA TTCATTCATT CATTCATTCA TTCATTCACC
ATGGAGTCTG TGTTCCCT[6]GT GACCTGCACT CGGAAGCC[4]CT
GTGTACAGGG GACTGTGTGG GCCAGGCTGG ATAA[2]TCGGGA GCTTTTCAGC
CCACAGGAGG GGTCTTCGGT GCCTCCTTGG GCACTCAGAA CCTTGGGCTC
CCTGGCACAT TTAAAATGGG TTTTTATTTA TGGACCTTGA TTGAAATGTG
GTGTGAGTTG TAGCAGTGTC ATTTCCAGGT ACCTTCTCAG GGACACAGGG
CGCCCTCCCC CGTCCTCCCC CGCCCTCCCC TACCCTCCCC CACCAGGCTC
CCCATC

FIG. 1

$E_I$ allele $E_P$ allele

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

GGCAAATAGG GGGCAAAA                                                     18

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

TTATCCAGCC TGGCCCAC                                                     18

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GGCAAATAGG GGGCAAAA                                                     18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GGCTTCCGAG TGCAGGTC                                                     18

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
GTTCCTCCCT TATTTCCC                                                          18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AGGGAACACA GACTCCAT                                                          18

(2) INFORMATION FOR SEQ ID NO:7:

(i) SEQUENCE CHARACTERISTICS:
        (A) LENGTH: 636 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

CTTGAATCTT AACGATCGGA ATGTGGAAAC AAATCCATCC AAAAAATCCA AGATGGCCAG             60

AGGTCCCCGG CTGCTGCACC CAGCCCCCAC CCTACTCCCA CCTGCCCCTG CCTCCCTCTG            120

CCCCAGCTGC CCTAGTCAGC ACCCCAACCA GCCTGCCTGC TTGGGGAGGC AGCCCCAAGG            180

CCCTTCCCAG GCTCTAGCAG CAGCTCATGG TGGGGGGTCC TGGGCAAATA GGGGGCAAAA            240

TTCAAAGGGT ATCTGGGCTC TGGGGTGATT CCCATTGGCC TGTTCCTCCC TTATTTCCCT            300

CATTCATTCA TTCATTCATT CATTCATTCA TTCATTCACC ATGGAGTCTG TGTTCCCTGT            360

GACCTGCACT CGGAAGCCCT GTGTACAGGG GACTGTGTGG GCCAGGCTGG ATAATCGGGA            420

GCTTTTCAGC CCACAGGAGG GGTCTTCGGT GCCTCCTTGG GCACTCAGAA CCTTGGGCTC            480

CCTGGCACAT TTAAAATGGG TTTTTATTTA TGGACCTTGA TTGAAATGTG GTGTGAGTTG            540

TAGCAGTGTC ATTTCCAGGT ACCTTCTCAG GGACACAGGG CGCCCTCCCC CGTCCTCCCC            600

CGCCCTCCCC TACCCTCCCC CACCAGGCTC CCCATC                                     636
```

METHOD FOR DIAGNOSING SCHIZOPHRENIA

The present invention relates to a method for diagnosing schizophrenia. It relates, more particularly, to a process for detecting variations in a repeated DNA sequence which is present in the TH gene, certain forms of which appear specifically in schizophrenic patients. The invention also relates to primers which can be used for detecting specific alleles of this repeated sequence, which alleles are associated with schizophrenia.

The presence of mutations in all classes of repeated DNA sequences is a known phenomenon. However, the functional significance of these mutations is unknown. Thus, microsatellites represent an abundant class of repeated DNA sequences which exhibit a high degree of polymorphism linked to variations in the number of repeated motifs (ref. 1) and/or in the sequence of these motifs. For this reason, these microsatellites have been used as genetic markers for constructing genetic maps and for identifying loci which are involved in pathologies (ref. 2). The size of the different alleles of a microsatellite depends on variations in the number of repeated motifs. Thus, sequencing experiments carried out on repeated dimers have demonstrated a variation in the number of repeated motifs and in their sequence. These variations can correspond, in particular, to "perfect" repeats, that is to say without interruption in the base sequence, or to "imperfect" repeats, which contain one or more interruptions in the sequences of the motifs, which interruption(s) can be (a) deletion(s) or (an) insertion(s) (ref. 3). In the same way, variations in length and/or sequence have also been observed in the repeated trimeric or tetrameric motifs. Thus, variations of this type have been observed in the HUMHPRTB (ref. 4) and HUMTH01 (ref. 5) microsatellites.

The Applicant has been interested, more particularly, in searching for genetic alterations which are linked to schizophrenia. To this end, the Applicant has carried out a study of the association between the gene for tyrosine hydroxylase (TH) and schizophrenia, which study has been orientated more particularly towards the HUMTH01 microsatellite. TH is the limiting enzyme in the pathway for biosynthesizing catecholamines. Various genetic studies of psychiatric and neurological pathologies have been carried out using markers which are located in the TH gene (refs 6 and 7). However, there has so far been no demonstration in the literature of a genetic association with schizophrenia.

The HUMTH01 microsatellite is located in the first intron of the tyrosine hydroxylase gene. This microsatellite consists of repeated tetrameric TCAT motifs. It exhibits a certain degree of polymorphism, with different alleles possessing variable numbers of repeated motifs having been described. The allele which is most frequently encountered comprises 10 repeated motifs and a deletion of one base pair in the fifth repeated motif, which motif has the sequence CAT.

The Applicant has consequently examined the involvement of the TH gene in schizophrenia by looking for the presence of sequence and length variations in the HUMTH01 microsatellite. The results which were obtained showed that the perfect allele was very rare and was only present in schizophrenic patients. These results were replicated in patient populations of different ethnic origin. Thus, 6 different alleles, designated A, B, C, D, Ei and Ep, were detected in a French population of 239 subjects, 94 of which were suffering from schizophrenia. These different alleles differ from each other by 4 base pairs (1 complete motif), with the exception of the two longest alleles, which differ by one single base pair. Sequencing these different alleles demonstrated that the repeated motif of the HUMTH01 microsatellite, having the sequence TCAT, is perfectly repeated in the A, B, C and D alleles, which respectively contain 6, 7, 8 and 9 repeated motifs. On the other hand, the E allele, which comprises 10 repeat motifs, exhibits the same deletion of one thymidine in the fifth repeated motif in the majority of cases. This deletion results in an imperfect allele, which has the sequence (TCAT)4(CAT)(TCAT)5 and is designated Ei (for imperfect). The Ei allele is the allele which is most frequently found in the Caucasian population (ref. 5). By contrast, the perfect E allele, having the sequence (TCAT)10 (designated Ep), is very rare. Thus, of the entire schizophrenic population which was tested, only 5 patients possessed the perfect allele. The results which were obtained unexpectedly demonstrate that all the subjects harbouring the Ep allele are schizophrenic patients, whereas this allele is not present in 145 healthy control subjects (cf. Table 1). These results demonstrate a highly significant association between the presence of the Ep allele and schizophrenia. Furthermore, the 5 schizophrenic patients harbouring the Ep allele are sporadic cases of schizophrenia whose clinical subtype is a paranoid schizophrenia in one case, an undifferentiated schizophrenia in 3 cases and a disorganized schizophrenia in 1 case.

The Applicant then extended this study to another population of different ethnic origin. Thus, a similar association study was undertaken on a population of 88 Tunisians. The results obtained demonstrate that the frequency of the different A–E alleles encountered in the Tunisian population tested is significantly different from that observed in the French population (cf. Table 1). Nevertheless, only 4 individuals proved to harbour the perfect Ep allele, with all these individuals being schizophrenic patients (1 paranoid schizophrenia and 3 undifferentiated schizophrenias); the schizophrenic forms were sporadic forms in this instance as well.

These results constitute the first demonstration of an association between TH and schizophrenia. They clearly demonstrate that the perfect Ep allele of the HUMTH01 microsatellite, having the sequence (TCAT)10, can be significantly associated with schizophrenia and for this reason represents a genetic tool for screening for this type of pathology.

The specific nature of the association of this allele with schizophrenia has furthermore been confirmed by a study on a population of 100 patients suffering from sporadic manic-depressive psychosis. The Ep allele was not found to be present in any of these patients.

The demonstration of the association between this allele and schizophrenia offers a large number of applications in the diagnostic and therapeutic fields. Thus, the present invention now offers, for the first time, the possibility of diagnosing schizophrenia by means of a biological test and no longer exclusively by means of clinical reasoning. One part of the subject-matter of the present invention is, more particularly, a method for diagnosing schizophrenia, which method consists in detecting the presence of the Ep allele of the HUMTH01 microsatellite in the TH gene. This method can also be applied to diagnosing pathologies of the schizophrenia spectrum, such as, in particular, schizotypy, schizoid individuals, etc. The invention thus makes it possible to refine the criteria for diagnosing these pathologies, which criteria are currently solely of a clinical nature. Furthermore, the invention also makes it possible to demonstrate predispositions to this type of psychiatric disorder by means of identifying a genetic vulnerability in the families of patients which harbour this Ep allele. From a therapeutic point of view, the invention advantageously makes it possible to define medical treatments which are more appropriate in terms of the type of schizophrenia. By confirming the hypothesis of an involvement of the catecholamine pathway, the invention makes it possible to use therapies which are more targeted. Furthermore, even if the functional implications of the presence of the Ep allele have not been definitely established, it is to be noted that the HUMTH01 microsatellite is located in the first intron of the TH gene, that is the region in which alternative splicing, leading to 4 isoforms of TH, has been demonstrated (ref. 8). It is therefore possible that genetic variations in this region affect regulation of the expression of the TH gene and that this is linked to the appearance of schizophrenia.

According to a first aspect, the invention therefore relates to a method for diagnosing schizophrenia, which method is characterized by detecting in vitro the presence of the Ep allele of the HUMTH01 microsatellite in the TH gene. The demonstration of this allele, having the sequence (TCAT)10, is characteristic of certain schizophrenias. The absence of this allele does not exclude the existence of a schizophrenia, since this allele is encountered in approximately 5% of cases. The process of the invention can also be applied to the genetic characterization of schizophrenias and to schizophrenia subtyping. As previously indicated, the Ep allele only appears to be present in sporadic schizophrenias. The process of the invention can also be applied to demonstrating predisposition to schizophrenia.

In the process of the invention, the Ep allele can be detected by a variety of techniques. The usable techniques which may preferably be cited are sequencing, gel separation or alternatively the SSCP technique.

Any sequencing method known to the skilled person may be employed. In particular, it is advantageous to use an automated DNA sequencer. The sequencing is preferably carried out on double-stranded templates by means of the chain-termination method using fluorescent primers. An appropriate kit for this purpose is the Taq Dye Primer sequencing kit from Applied Biosystem (Applied Biosystem, Foster City Calif.). Sequencing the HUMTH01 microsatellite, or more precisely an isolated fragment carrying this microsatellite, makes it possible to identify directly the allele which is present in the patient and thus to demonstrate the presence or absence of the Ep allele having the sequence (TCAT)10. The results obtained by sequencing are presented in FIG. 2 by way of example.

Figure 3:
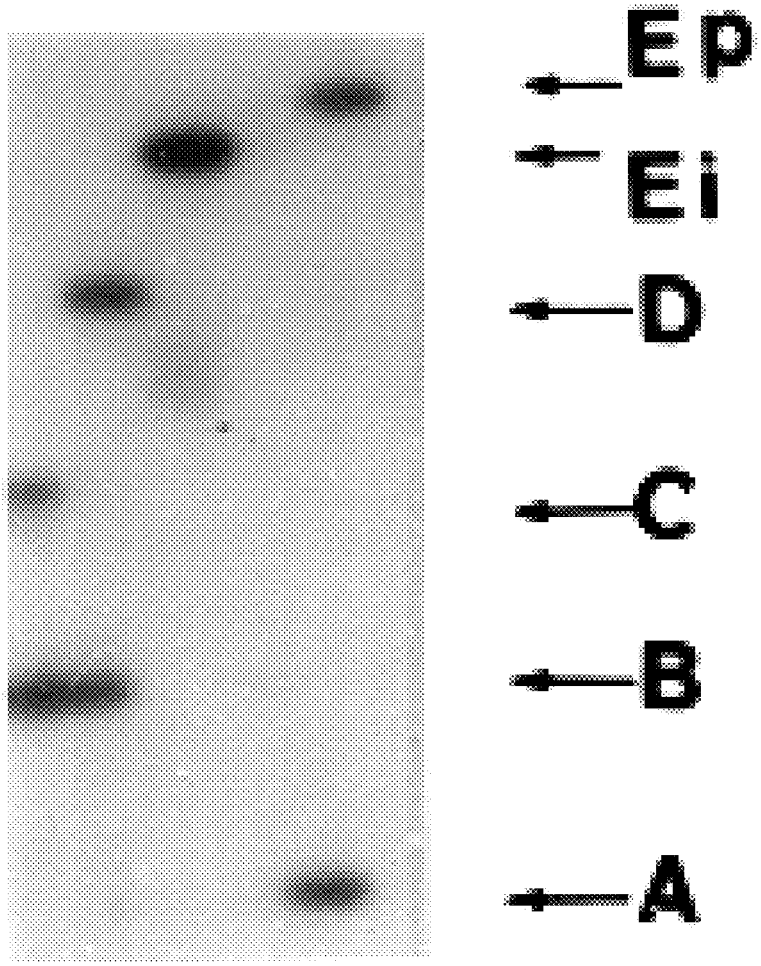

A preferred technique for demonstrating the Ep allele is that of separation on a gel. This technique has the advantage of making it possible to discriminate between the different alleles in terms of their size without it being necessary to sequence the DNA fragments. This technique is based on the migration, under denaturing conditions, of the denatured DNA fragments in a (preferably 6%) acrylamide gel. The bands can be visualized by any technique known to the skilled person, with the technique being based, for example, on using labelled primers (in particular in the γ position on the phosphorus), on introducing α-dCTP into the tested fragments, on the α (alpha) use of cold probes, or on visualizing with ethidium bromide or else by means of hybridization (blotting) with a radiolabelled probe. A specific protocol for gel separation is given in the examples by way of illustration. As indicated in FIG. 3, this technique makes it possible to distinguish rapidly, and without sequencing, between the A, B, C, D, Ei and Ep alleles of the microsatellite.

The SSCP identification technique is also a method involving separation on an acrylamide gel, but under non-denaturing conditions. This technique makes it possible to discriminate between the different fragments in terms of their conformation (cf. examples).

The process of the invention is carried out on a DNA sample from the patient. This sample should at least contain the HUMTH01 microsatellite. It preferably contains all or part of the first intron of the TH gene. Even more preferably, it comprises a fragment of the TH gene containing the HUMTH01 microsatellite bordered by flanking sequences. The DNA sample to be tested can be obtained from cells which have been withdrawn from the patient. These cells are preferably blood cells (for example mononucleated cells), which are easily obtained by the simple withdrawal of blood. Other cell types, such as, in particular, fibroblasts, epithelial cells, keratinocytes, etc., can be employed. The DNA is then extracted from the cells and used to detect the Ep allele. For this, the genomic DNA which has been obtained can be digested with restriction enzymes, cloned into appropriate vectors, selected for TH, for example, or by means of hybridization with a probe corresponding to the first intron of TH, then analysed as described above. Most preferably, the DNA extract is initially subjected to one or more amplification reactions in order to obtain a substantial quantity of material corresponding to the region carrying the HUMTH0 microsatellite. The amplification can be effected by any technique known to the skilled person, and in particular by means of the so-called PCR technique [ Polymerase-catalyzed Chain Reaction, Saiki R. K. et al., Science 230 (1985) 1350–1354; Mullis K. B. et Faloona F. A., Meth. Enzym. 155 (1987) 335–350]. In this regard, the amplification can be effected using a DNA thermal cycler (Perkin Elmer Cetus) in accordance with the manufacturer's specifications. The temperature and medium conditions used for the amplification are the general conditions as described, for example, in Maniatis et al., 1989. Specific conditions are also given in the examples. For the purpose of implementing the present invention, it is advantageous to use a DNA fragment carrying the HUMTH01 microsatellite which is of a sufficiently small size. This advantageously makes it possible to discriminate between the alleles without having to resort to sequencing. Furthermore, if control sequencing experiments are carried out, it is also preferable only to have fragments of limited size to sequence. Advantageously, the DNA fragment employed is an amplified fragment of a size which is less than 300 bp. This fragment carries the HUMTH01 microsatellite and flanking sequences of the TH gene, as depicted in FIG. 1. Even more preferably, the amplified fragment comprises less than 200 bp. Particularly noteworthy results have been obtained with amplified fragments of a size less than 160 bp and even of less than 100 bp. To this end, the present invention also describes specific primers which make it possible to amplify DNA fragments which are of small size and which carry the HUMTH01 microsatellite. Thus, the invention describes, in particular, 3 pairs of primers which make it possible to amplify fragments of 192 bp, 156 bp and 77 bp, respectively. The sequence of these primers is given in the examples, as are the sequence and the position on the TR gene of the amplified fragment. Any other primer which makes it possible to amplify a fragment of less than 300 bp carrying at least the HUMTH 01 microsatellite and a flanking region, which region is derived from the sequence depicted in FIG. 1, also forms part of the present invention. Advantageously, the primers according to the invention have a length of between 10 and 40 mer, preferably of between 15 and 30 mer. The sequence of these primers can be determined from the sequence given in FIG. 1, in dependence on the size of the amplified fragment, on its location around the microsatellite and on the chosen length of the primers.

The primers which are used wi thin the context of the invention can be synthesized by any technique known to the skilled person, and in particular using phosphoramidite chemistry, with the phosphoramidites being protected, if necessary, in the β position by a cyanoethyl group (Sinha et al;, 1984, Giles 1985), employing an automated DNA synthesizer, such as the Applied Biosystem model 394 synthesizer (Applied Biosystem, Foster City Calif.), in accordance with the manufacturer's recommendations. The primers can also be labelled by any technique known to the skilled person.

The DNA sample to be tested can be a genomic DNA or a cDNA, or equally an RNA. It is more preferably the genomic DNA amplification product, which has been amplified using specific primers as described above.

The invention also relates to a kit for detecting the Ep allele, with the kit comprising a pair of primers as defined above. This kit is advantageously a kit for diagnosing schizophrenia.

As previously indicated, the present invention provides, for the first time, a genetic method for detecting and genetically characterizing diseases of the schizophrenic spectrum. Apart from the diagnostic applications mentioned, this method also offers important therapeutic possibilities which are linked, in particular, to improved targeting of the treatment in accordance with the ailment concerned.

The present invention will be described in more detail with the aid of the following examples, which should be regarded as being illustrative and not limiting.

List of Figures

FIG. 1: sequence of a part of the first intron of the TH gene including the HUMTH01 microsatellite. The position of the amplification primers is indicated.

Figure 2B:
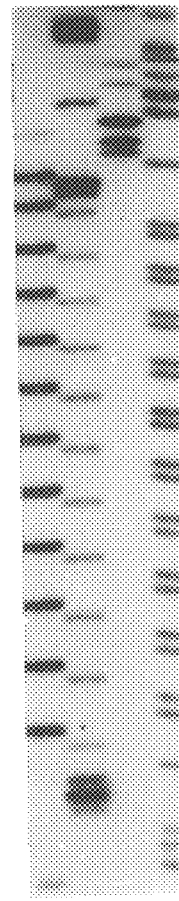

FIG. 2: demonstration by sequencing of the Ep allele of the HUMTH01 microsatellite.

FIG. 3: demonstration by gel separation of the Ep allele of the HUMTH01 microsatellite.

Table 1: distribution of the alleles of the HUMTH01 microsatellite in tested populations which are or are not suffering from schizophrenia.

EXAMPLES

1. Preparation of the DNA

The blood samples were collected onto heparin and the mononucleated cells were isolated on a Ficoll hypaque gradient (Pharmacia, Upsala, Sweden). The DNA was then extracted using standard techniques. The following protocol was used for extracting the DNA directly:

The blood which had been collected was poured into 50 ml tubes and lysis buffer was added in order to rupture the red blood cells (LYSIS BUFFER=40 ml of 1N TRIS/HCl, pH 7.5+20 ml of 0.5M EDTA+milliQ $H_2O$ to make up to 2 L), final volume: 50 ml. The suspension is then centrifuged at 2500 rpm for 15 ms at 4° C.; the supernatant is discarded and 50 ml of lysis buffer are added once again to the pellet. The same operation (centrifugation, elimination of the supernatant and taking up the pellet in lysis buffer) is repeated twice. The pellet is recovered at the conclusion of these 3 centrifugations.

| The following are then added: | 5 ml of lysis buffer (per 5 ml of original blood) 125 µl of 20% lauroylsarcosine 50 µl of proteinase K (20 ng/ml) |
|---|---|

The resulting solution is mixed and placed overnight in a stirred water bath at 55° C.

The following morning, 2 volumes of 95% ethanol are added (if 5 ml→15 ml final volume) and the solution is then precipitated by inverting until a flocculate is formed. The DNA is then recovered using a P1000 pipette (with the end of the cone truncated) in a 5 ml tube. 80% ethanol is then added and the mixture is placed in a refrigerator. The ethanol is changed on the following morning and the alcohol is then removed in the evening and the flocculate is left to dry (the tube is left inverted on a piece of tissue).

The DNA is then dissolved in 1×TE; depending on the size of the flocculate, the quantity of TE varies from 200 µl to 1 ml. The mixture is left overnight on a rotator at 37° C. and the DNA concentration is then determined by spectrometry.

2. French Population:

94 patients who were of differing origin and who were suffering from chronic schizophrenia (62 men and 32 women, mean age 42±12.3), including 21 familial cases, were studied. The diagnosis was formulated in accordance with the DSM III criterion (ref. 9) using data derived from medical tables and direct interview in accordance with the French translation of the Table of Affective Disorders and of Schizophrenic Anxiety (SADSLA, ref. 10). A clinical subtype was assigned to each patient in accordance with the described procedure. 145 non-apparent control subjects, who were not exhibiting any psychiatric disorder, were studied (84 men and 61 women; mean age 48±8.3).

3. Tunisian Population:

44 patients who were of differing origin and who were suffering from chronic schizophrenia (33 men and 11 women, mean age 37±8.2), including 13 familial cases, were studied. The diagnosis was formulated in accordance with the DSM IIIR criterion (ref. 11) using data derived from medical tables. These patients were compared with 44 unrelated control patients who were not exhibiting any psychiatric disorder (37 men and 7 women; mean age 35±5.9).

4. Primers used for the Amplification Reactions

The targeted template for the amplification reactions consists of the Ep allele of the HUMTH01 microsatellite, the sequence of which allele is (TCAT)4TCA(TCAT)5. The microsatellite is located at position 1070 of the sequence of the TH gene as published and is accessible in Genebank (No. D00269).

Different pairs of primers were used for the PCR amplification. These pairs are given below as is the size of the amplified fragment. The position of these primers on the sequence of the TH gene is given in FIG. 1 (see SEQ ID No.1 as well).

Pair A:
1) 5'GGC AAA TAG GGG GCA AAA 3'(sense)(SEQ ID No.1) and
2) 5'TTA TCC AGC CTG GCC CAC 3'(antisense)(SEQ ID No.2), The expected amplification length is 192 bp.

Pair B:
3) 5'GGC AAA TAG GGG GCA AAA 3'(sense)(SEQ ID No.3) and
4) 5'GGC TTC CGA GTG CAG GTC 3'(antisense)(SEQ ID No.4).

The expected amplification length is 156 bp.

Pair C:
5) 5'GTT CCT CCC TTA TTT CCC 3'(sense)(SEQ ID No.5) and
6) 5'AGG GAA CAC AGA CTC CAT 3'(antisense)(SEQ ID No.6).

The expected amplification length is 77 bp.

5. Protocol for the Amplification Reactions

The mixture employed for the PCR reaction contains: 40 ng of genomic DNA prepared as described in Example 1, 200 mM of each of dATP, dCTP, dGTP and dTTP, 18 pmol (100 ng) of each primer, 50 mM KCl, 10 mM Tris/HCl (pH 8.5), 1.5 mM MgCl and 1.0 mCi of (a-$^{32}$P) dCTP (Amersham, UK) in a final volume of 15 ml.

After an initial denaturation at 96° C. for 3 min, 0.75 units of Taq polymerase are added to each sample (DNA+mix) at 92° C.; this step is followed by 30 cycles comprising hybridization for 30" at 56° C., elongation for 30" at 72° C. and denaturation for 30" at 92° C.

6. Gel Separation

Three microlitres of the PCR reaction product mixed with 3 microlitres of stop solution (0.025 of bromophenol blue and 0.025 of xylene cyanole, and 0.95 of deionized formamide) are loaded into a denaturing gel (6% acrylamide/bisacrylamide 19:1). Following electrophoretic migration (2500 volts, 55 mA), the gel is removed and dried. It is placed in a cassette (without intensifying screen) together with an autoradiographic XOMAT (Kodak) film and exposed overnight at ambient temperature.

7. Protocol for the PCR-SSCP Reaction

This reaction was carried out in several steps in accordance with the following protocol:

1-PCR (Polymerase Chain Reaction) amplification of the target DNA sequence (150–200 bp) with radioactive labelling of the double strands (use of $\alpha$-$^{32}$P-ATP) or of a single strand (kination of one of the primers with $\gamma$-$^{32}$P-ATP).

One ml of PCR product is mixed with 2.5 ml of loading buffer (80% deionized formamide, 50 mM TBE, 1 mM EDTA, 0.5% xylene cyanole, 0.5% bromophenol blue).

2-Denaturation of the DNA at 96° C. for 3–5 min.

3-Rapid cooling of the samples in melting ice.

4-Rapid deposition in a non-denaturing polyacrylamide gel (6% acryl/bisacrylamide 37.5:1, 0.5×TBE).

5-Electrophoretic migration at 4° C. and 50 W or at ambient temperature and 10 W (with 10% glycerol in the gel).

6-Autoradiography of the dried gel.

TABLE 1

| ALLELE | FRANCE** CONTROL SUBJECTS[a] | SCHIZOPHRENIC SUBJECTS[b] | TUNISIA CONTROL SUBJECTS[a] | SCHIZOPHRENIC SUBJECTS |
|---|---|---|---|---|
| A(tcat)6 | 54 (18.6%) | 40 (21.3%) | 20 (22.7%) | 18 (20.5%) |
| B(tcat)7 | 54 (18.6%) | 43 (22.9%) | 20 (22.7%) | 20 (22.7%) |
| C(tcat)8 | 38 (13.1%) | 18 (9.6%) | 14 (15.9%) | 8 (9.1%) |
| D(tcat)9 | 52 (17.9%) | 23 (12.2%) | 21 (23.9%) | 26 (29.5%) |
| EI(tcat)4cat(tcat)5 | 92 (31.8%) | 58 (30.8%) | 13 (14.8%) | 12 (13.6%) |
| Ep(tcat)10 | 0 (0%) | 6** (03.2%) | 0 (0%) | 4 (4.6%) |

List of References

1. Weber et al., Am. J. Hum. Genet. 44 (1989) 388
2. Hearne et al., Trends Genet. 8 (1992) 288
3. Weber et al., Genomics 7 (1990) 524
4. Edwards et al., Genomics 12 (1992) 241
5. Puers et al., Am. J. Hum. Genet. 53 (1993) 953
6. Craddock et al., Ann. of Medecine 25 (1993) 317
7. Leboyer et al., Lancet 335 (1990) 1219
8. Grima et al., Nature 326 (1987) 707
9. American Psychiatric Association, Diagnostic and Statistical Manual of mental disorders (3rd Edn)—Washington, D.C.=APA (1980).
10. Fyer et al., Anxiety Disorders clinic, New York: New-York State Psychiatric Institute (1985).
11. American Psychiatric Association, Diagnostic and Statistical Manual of mental disorders (3rd Edn revised)—Washington, D.C.=APA (1987).

What is claimed is:

1. A method for diagnosing schizophrenia, comprising
   a) obtaining from a patient a DNA sample comprising the HUMTH01 microsatellite in the tyrosine hydroxylase (TH) gene; and
   b) identifying the HUMTH01 microsatellite allele present in the patient, wherein detection of a perfect allele (Ep) of the HUMTH01 microsatellite is an indication that said patient may suffer from schizophrenia.

2. The method according to claim 1, wherein the HUMTH01 microsatellite allele is detected by sequencing.

3. The method according to claim 1, wherein the HUMTH01 microsatellite allele is detected by gel separation.

4. The method according to claim 1, wherein the HUMTH01 microsatellite allele is detected by a single strand conformational polymorphism (SSCP) method.

5. The method according to claim 1, wherein the DNA is extracted from mononucleated cells of said patient.

6. The method according to claim 1, wherein the DNA is amplified prior to detection.

7. The method according to claim 6, wherein the amplified DNA comprises part of a first intron of the TH gene.

8. The method according to claim 6, wherein the amplified DNA is less than 300 bp in size, and comprises the HUMTH01 microsatellite and flanking sequences.

9. The method according to claim 8, wherein the amplified DNA is less than 200 bp in size.

10. The method according to claim 9, wherein the amplified DNA is less than 100 bp in size.

11. The method according to claim 1, further comprising diagnosing schizophrenia according to clinical criteria.

12. A method for demonstrating a predisposition to schizophrenia, comprising
    a) obtaining from a patient a DNA sample comprising the HUMTH01 microsatellite in the tyrosine hydroxylase (TH) gene; and
    b) identifying the HUMTH01 microsatellite allele present in the patient, wherein detection of a perfect allele (Ep)

of the HUMTH01 microsatellite is an indication of a predisposition to schizophrenia in said patient.

13. The method according to claim 12, wherein the HUMTH01 microsatellite allele is detected by sequencing.

14. The method according to claim 12, wherein the HUMTH01 microsatellite allele is detected by gel separation.

15. The method according to claim 12, wherein the HUMTH01 microsatellite allele is detected by a single strand conformational polymorphism (SSCP) method.

16. The method according to claim 12, wherein the DNA is extracted from mononucleated cells of the patient.

17. The method according to claim 12, wherein the DNA is amplified prior to detection.

18. The method according to claim 17, wherein the amplified DNA comprises part of a first intron of the TH gene.

19. The method according to claim 17, wherein the amplified DNA is less than 300 bp in size, and comprises the HUMTH01 microsatellite and flanking sequences.

20. The method according to claim 19, wherein the amplified DNA is less than 200 bp in size.

21. The method according to claim 20, wherein the amplified DNA is less than 100 bp in size.

* * * * *